(12) United States Patent
Slaski

(10) Patent No.: US 11,259,969 B2
(45) Date of Patent: Mar. 1, 2022

(54) WELTED TEXTILE ORTHOSIS

(71) Applicant: LABORATOIRES INNOTHERA, Arcueil (FR)

(72) Inventor: Jean-Pierre Slaski, Brantigny (FR)

(73) Assignee: LABORATOIRES INNOTHERA, Arcueil (FR)

( * ) Notice: Subject to any disclaimer, the term of this patent is extended or adjusted under 35 U.S.C. 154(b) by 972 days.

(21) Appl. No.: 15/388,599

(22) Filed: Dec. 22, 2016

(65) Prior Publication Data

US 2017/0172808 A1   Jun. 22, 2017

(30) Foreign Application Priority Data

Dec. 22, 2015 (FR) ..................... 15 63141

(51) Int. Cl.
| | | |
|---|---|---|
| *A61F 13/08* | (2006.01) | |
| *D04B 1/10* | (2006.01) | |
| *D04B 1/26* | (2006.01) | |
| *A61F 13/00* | (2006.01) | |
| *D04B 9/00* | (2006.01) | |

(52) U.S. Cl.
CPC ........ *A61F 13/08* (2013.01); *A61F 13/00987* (2013.01); *D04B 1/106* (2013.01); *D04B 1/265* (2013.01); *D04B 9/00* (2013.01); *A61F 2013/0028* (2013.01); *A61F 2013/00238* (2013.01)

(58) Field of Classification Search
CPC .............. A61F 13/08; A61F 13/00987; A61F 2013/0028; A61F 2013/00238; A41B 11/003; A41B 11/12; A41B 11/02; A41B 11/04; A41B 11/121; A41B 11/123; A41B 11/125; D04B 9/00
See application file for complete search history.

(56) References Cited

U.S. PATENT DOCUMENTS

| | | | | |
|---|---|---|---|---|
| 3,729,956 A | * | 5/1973 | Nebel | D04B 1/26 66/172 E |
| 3,908,407 A | * | 9/1975 | Brand | D04B 1/26 66/172 E |
| 3,975,929 A | * | 8/1976 | Fregeolle | D04B 1/18 602/63 |
| 3,983,870 A | * | 10/1976 | Herbert | A41B 11/12 602/63 |

(Continued)

FOREIGN PATENT DOCUMENTS

| | | |
|---|---|---|
| EP | 1 878 822 A1 | 1/2008 |
| FR | 835 383 A | 12/1938 |

(Continued)

OTHER PUBLICATIONS

Oct. 19, 2016 Search Report issued in French Patent Application No. 1563141.

*Primary Examiner* — Camtu T Nguyen

(74) *Attorney, Agent, or Firm* — Oliff PLC

(57) ABSTRACT

An orthosis chosen from a venous support orthosis and an elastic venous compression orthosis, the orthosis including a ribbed top and a leg part, the ribbed top including an intermediate part extending the leg part, the stitch being different on each side of the boundary separating the leg part and the intermediate part, a welt extending the intermediate part and of a height less than 1.5 cm.

17 Claims, 2 Drawing Sheets

(56) References Cited

U.S. PATENT DOCUMENTS

| | | | | |
|---|---|---|---|---|
| 4,630,455 A * | 12/1986 | Lingenfelter | .......... | D04B 1/106 |
| | | | | 2/239 |
| 5,016,450 A * | 5/1991 | Pernick | .................... | D04B 1/02 |
| | | | | 66/194 |
| 5,617,745 A * | 4/1997 | Della | .................. | A41B 11/003 |
| | | | | 2/239 |
| 6,739,160 B1 * | 5/2004 | Hiraga | .................... | D04B 1/22 |
| | | | | 66/170 |
| 6,871,516 B2 * | 3/2005 | Peeler | .................... | D04B 1/106 |
| | | | | 66/171 |
| 7,076,973 B1 * | 7/2006 | Chesebro, Jr | .......... | A41B 11/00 |
| | | | | 2/239 |
| 2010/0100024 A1 * | 4/2010 | Reid, Jr. | ................ | A61F 13/08 |
| | | | | 602/63 |
| 2015/0245951 A1 * | 9/2015 | Convert | ................ | D04B 1/265 |
| | | | | 66/178 A |

FOREIGN PATENT DOCUMENTS

| | | | |
|---|---|---|---|
| FR | 2 957 783 A1 | | 9/2011 |
| FR | 2 995 525 A1 | | 3/2014 |
| GB | 2 260 343 A | * | 10/1991 |
| GB | 2 260 343 A | | 4/1993 |
| WO | 2010/092306 A1 | | 8/2010 |

\* cited by examiner

WELTED TEXTILE ORTHOSIS

TECHNICAL FIELD

The present invention relates to a venous support and/or elastic venous compression, or EVC, orthosis, hereinafter referred to as an "orthosis", which is prescribed for patients with venous disorders of the lower limb.

PRIOR ART

Such an orthosis is a textile medical device that produces a therapeutic effect by supporting and/or compressing the lower limbs, as opposed to a "control types" (or even "support types" or "anti-fatigue types") and "fashion types" which are not medical devices with a therapeutic use.

The end part of the orthosis, which defines the opening via which it is put on, may comprise a ribbed top. A ribbed top, which is extensible in the circumferential direction, conventionally has the role, once the orthosis has been put onto the limb, of locally applying a textile pressure to hold the orthosis in position. WO 2010/092306 A1, by Laboratoires Innothéra, proposes a modelling of the various factors that contribute to this retention:

The ribbed top generally takes the form of a welt, as described in U.S. Pat. No. 6,871,516 or in FR 2 957 783. However, the welt leads to a discontinuity in the pressure profile, and this detracts from comfort.

FR 2 995 525 proposes a weltless ribbed top, merely modifying the pattern of the knit. When manufactured on a conventional knitting machine of the "single cylinder" type, such a ribbed top has a very high tendency to roll over on itself, thus creating a source of discomfort, of risk to blood circulation and of poor hold on the wearer. It is therefore necessary to resort to special-purpose knitting machines, such as circular knitting machines of the "double bed" type. Such special-purpose knitting machines do not allow the knitting of fine-textured orthoses.

On a circular knitting machine, the "gauge" denotes the number of needles per inch along the arc of the cylinder. Conventionally, the gauge of a circular knitting machine of the "double bed" type is around 10 to 15. For a fine texture, the gauge is preferably greater than 20, or even greater than 25.

It is an object of the invention to provide an orthosis that makes it possible, at least in part, to solve the abovementioned problems.

SUMMARY OF THE INVENTION

According to the invention, this object is achieved by means of an orthosis chosen from a venous support orthosis and an elastic venous compression orthosis, the said orthosis comprising a ribbed top and a leg part, the ribbed top comprising
- an intermediate part extending the leg part, the stitch being different on each side of the boundary separating the leg part and the intermediate part,
- a welt extending the intermediate part and of a height less than 1.5 cm.

The two functions of the ribbed top are therefore substantially separated and are performed by the welt and by the intermediate part, respectively: the key function of the welt is to prevent the orthosis from rolling up on itself, the low height of the welt not allowing it to play any significant part in holding the orthosis in position. The position retention function is chiefly assured by the intermediate part.

Advantageously, an orthosis according to the invention may have an aesthetic appearance comparable to that of "fashion" socks, and is particularly comfortable.

Furthermore, the presence of a welt means that it can be manufactured using conventional circular knitting machines of the "single cylinder" type, without this manufacture causing the ribbed top to roll up on itself. The use of a circular knitting machine of the "single cylinder" type advantageously allows the use of a gauge greater than 20, greater than 23, preferably greater than 25. Advantageously, the texture is particularly fine.

An orthosis according to the invention may further comprise one or more of the following optional and preferred features:
- the welt is knitted in such a way that on crossing the boundary from the intermediate part to the welt part, the textile pressure remains constant or decreases. Comfort is thereby advantageously improved;
- the structure of the welt is chosen so that the textile pressure exerted by the welt is lass than the pressure applied, on average per $cm^2$, by the leg part and/or by the intermediate part. Comfort is thereby advantageously improved;
- the welt has no weft inlay yarn or comprises a weft inlay yarn different from that of the intermediate part, and/or has a weft inlay yarn only in part of it, preferably only on one of the two bands of which it is made up. Advantageously, the textile pressure exerted by the welt may be thereby reduced, and comfort improved accordingly;
- the intermediate part is knitted with the same body knit and weft inlay yarns as the leg part and/or the welt is knitted with the same body knit yarn as the intermediate part. The manufacture of the orthosis is thereby advantageously simplified;
- the leg part and/or the ribbed top and/or the welt, preferably the orthosis, are manufactured using a circular knitting machine of the "single cylinder" type having a gauge greater than 20, the gauge being the number of needles along a cylindrical arc measuring one inch. Comfort is thereby advantageously improved,
- the orthosis is such that:
    - the leg part has a jersey stitch giving a smooth appearance; and
    - the intermediate part has a jersey stitch giving a ribbed pattern, preferably a 1×1 ribbed pattern and/or has a height greater than 3.0 cm.

The aesthetic appearance and comfort are thereby improved;
- the ratio
    - of the titre of the core of the weft inlay yarn of the intermediate part or, if the weft inlay yarn of the intermediate part is not wrapped, the titre of the weft inlay yarn of the intermediate part,
    - to the titre of the core of the weft inlay yarn of the welt or, if the weft inlay yarn of the welt is not wrapped, the titre of the weft inlay yarn,
    is greater than 2.0;
- the welt comprises a weft inlay yarn which is easier to deform than the weft inlay yarn of the intermediate part and/or of the leg part;
- the welt has a height less than 1.0 cm. Advantageously, the welt is more discrete, without that detracting from the comfort or effectiveness of the welt;
- the orthosis is of class I, II, III or IV according to the ASQUAL standard classification system;

the leg part, the intermediate part and the welt all comprise a body knit yarn made of elastane single wrapped or double wrapped with polyamide and a weft inlay yarn made of elastane double wrapped with polyamide.

The invention also relates to a method of manufacturing an orthosis according to the invention, in which use is made of a circular knitting machine of the "single cylinder" type.

BRIEF DESCRIPTION OF THE FIGURES

Further features and advantages of the invention will become further apparent from reading the detailed description which will follow and from studying the attached drawing in which.

In the figures, the same references are used to denote elements that are identical or functionally equivalent.

Definitions

The "service position" of an orthosis corresponds to a position of use, namely in which it is being worn on a lower limb of a patient.

A ribbed top is an extensible band of knitting at the upper end of the orthosis, the function of which is conventionally to hold the orthosis in the service position. Of course, the leg part also contributes to holding it in position. The elasticity of the ribbed top is adapted accordingly, in general, a person skilled in the art knows how to adapt the structure of a knit in order to increase or decrease the textile pressure, notably through the choice of stitch, of weft inlay yarn and of body knit yarn.

The pressure applied by an orthosis to any point is, according to Laplace's law, a pressure, referred to as a "textile pressure" within the meaning of French standard NF G30-102b, that is inversely proportional to the radius of curvature of the contour at that point. The textile pressure is conventionally evaluated in accordance with that standard. In the present description, unless indicated otherwise, a pressure refers to a "textile pressure", A "stitch" is a way of interlacing the body knit and weft inlay yarns.

DETAILED DESCRIPTION

Figure 1:
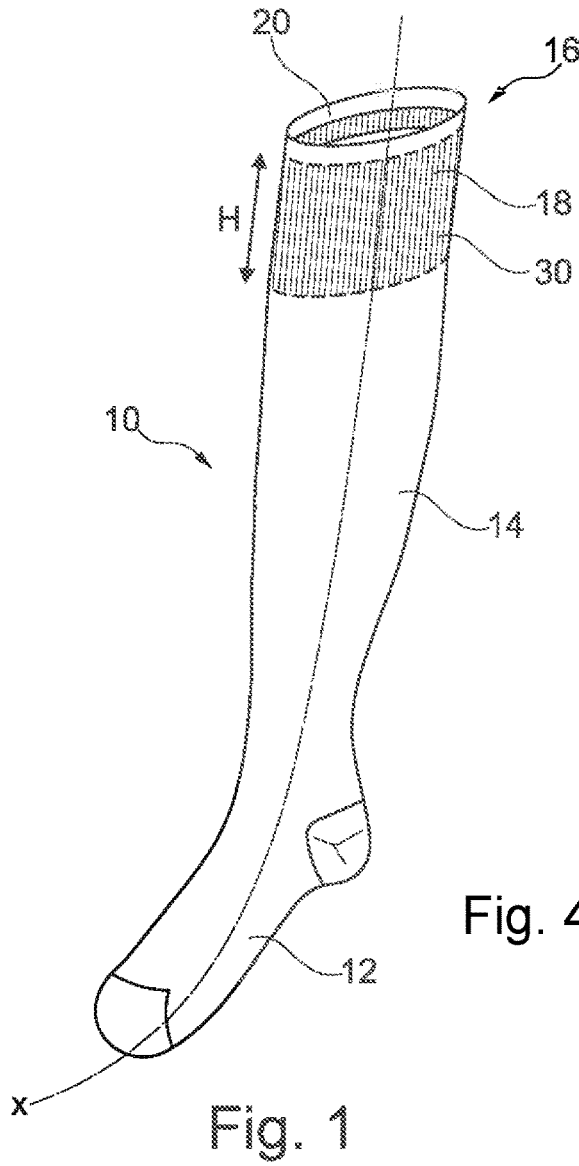
FIG. 1 schematically depicts an orthosis according to the invention.
Figure 2:
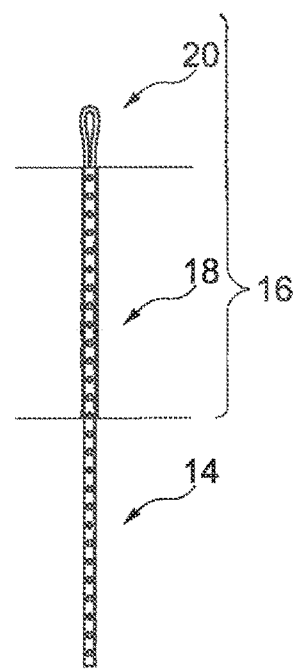
FIG. 2 depicts a view in cross section of the upper part of the orthosis of FIG. 1.

In FIGS. 1 and 2, the reference 10 denotes in general an orthosis according to the invention.

The orthosis 10 is an EVC orthosis.

EVC orthoses were formerly known by the names of "support stockings (or socks)" or "support tights".

The pressure profile applied by an orthosis usually decreases from the ankle upward.

According to the type of EVC orthosis, the pressure measured at the ankle may notably vary from 10 to over 36 mmHg (namely 13 to 45 hPa, although mmHg is in common usage as the unit for measuring pressure in the field of phlebology and medical compression).

A person skilled in the art knows how to select the stitch and the yarns and how to size the rows of stitches in order to apply a predetermined pressure profile at various heights at the lower limb.

EVC orthoses are divided, according to the ASQUAL standard classification system, into four textile classes, from class I (13 to 20 hPa≈10 to 15 mmHg at the ankle) to class IV (>48 hPa≈>36 mmHg at the ankle).

The invention is particularly well suited to an EVC orthosis.

Specifically, in order to allow the lower limbs to be compressed to a high pressure level that provides a therapeutic effect, an EVC orthosis is conventionally made from a knit stitch and, in the leg part, incorporates an elastic weft inlay yarn, generally made of a wrapped elastane.

Under the effect of the application of the orthosis to the patient's limb, the elastic yarn of the knit generates a return force which tends to cause the orthosis to slip down towards the foot.

The position-holding pressure exerted by the ribbed top therefore needs to be particularly high.

An orthosis according to the invention, like the one depicted in FIG. 1, preferably takes the form of a knee-high EVC sock, referred to as "knee-length" or "half-stocking" to the "AD" format, which means to say the ribbed top of which reaches to just below the knee when the orthosis is being worn. Externally it therefore has the same appearance as traditional "fashion" socks, but differs from these in terms of the choice of yarn and a knit that allows effective therapeutic compression to be obtained, preferably with a class-II compression.

The "Legger" (registered trademark) orthosis, designed and marketed by Laboratoires Innothéra, is an example of an EVC sock.

The orthosis may be "open-toed" or "closed-toed".

The orthosis 10, of anatomic overall shape, comprises
a foot part 12 which envelops the foot, extending from the toes as far as the malleolus bones, covering the instep,
a leg part 14 that is extensible in a longitudinal direction (namely in the main direction X) and in the circumferential direction (radial extensibility), extending from the malleolus region enveloping the ankle and the calf up to a level situated just below knee height; and
a ribbed top 16 extensible mainly in the circumferential direction and typically a knitted part.

According to the invention, the ribbed top 16 comprises an intermediate part 18 and a welt 20.

Figure 3:
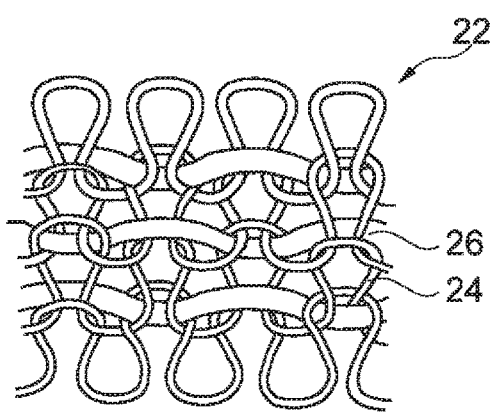
FIG. 3 illustrates one example of how the body knit yarns and weft inlay yarns are intertwined that can be applied to an orthosis according to the invention.

FIG. 3 illustrates one example of a stitch that can be used for the leg part 14 and/or the intermediate part 18.

This stitch corresponds to a "conventional" jersey knit. It comprises:
a network of stitches 22 created using a body knit yarn 24 or "knitting yarn", and
a weft inlay yarn 26, interlaced between the said body knit stitches and intended to exert an elastic pressure, for example an elastane or a mixture of elastane and of elasto-diene (synthetic rubber latex) which may be gimped (for example wrapped with polyamide) or ungimped.

In general, the nature of the threads and the type of stitch are adapted according to the action and appearance desired for the various parts of the orthosis. This adaptation presents no particular difficulties to those skilled in the art.

In one embodiment, the weft inlay yarns of the leg part, of the intermediate part and, where appropriate, of the welt are elastic. For preference, they contain elastane and/or an elasto-diene.

Foot Part

The foot part 12 may be produced using any known technique.

Leg Part

The leg part 14, once the orthosis has been put onto the limb, allows a compressive textile pressure to be applied to the leg at a therapeutic pressure level.

For this purpose, the leg part 14 is conventionally made from a knitted stitch incorporating an elastic weft inlay yarn, generally a wrapped elastane.

The stitch type and the yarns, as well as the sizing of the rows of stitches of the leg part, are chosen so as to apply predetermined pressures defined for each support/compression class at various heights up the leg, for example at ankle height, at the bottom of the calf, at the calf, etc.

In one preferred embodiment, the body knit yarn of the leg part is a simple wrapped thread made up of a core, preferably made of elastane, preferably wrapped with one or more covering threads made of polyamide and/or of cotton.

For preference, the titre (mass per unit length) of the core of the body knit yarn of the leg part is less than 30 dTex, preferably less than 25 dTex, preferably less than 20 dTex, and/or greater than 10 dTex, preferably greater than 15 dTex.

For preference, the titre of the gimping yarn covering the body knit yarn of the leg part is less than 60 dTex, preferably less than 50 dTex, preferably less than 45 dTex, and/or greater than 20 dTex, preferably greater than 30 dTex, preferably greater than 40 dTex.

For preference, the body knit yarn of the leg part is a yarn comprising a core made of 17 dTex elastane single wrapped with a 42 dTex polyamide yarn.

The weft inlay yarn 26 conventionally extends transversely with respect to the main direction X of the orthosis, indicated in FIG. 1. More specifically, it extends orthoradially, in a spiral around the main direction of the orthosis, passing along the rows of stitches.

In one preferred embodiment, the weft inlay yarn 26 is a wrapped yarn made up of a core, preferably made of elastane, preferably double wrapped with gimping yarns made of polyamide and/or cotton, preferably polyamide.

For preference, the titre of the core of the weft inlay yarn 26 is less than 350 dTex, preferably less than 330 dTex, preferably less than 320 dTex and/or greater than 250 dTex, preferably greater than 280 dTex, preferably greater than 290 dTex, preferably greater than 300 dTex.

For preference, the titre of the gimping yarn with which the weft inlay yarn 26 is wrapped is less than 40 dTex, preferably less than 30 dTex, preferably less than 25 dTex, and/or greater than 10 dTex, preferably greater than 15 dTex, preferably greater than 20 dTex.

For preference, the weft inlay yarn 26 is a yarn comprising a 310 dTex elastane core, double wrapped with a 22 dTex polyamide yarn.

Ribbed Top

The function of the ribbed top 16 is conventionally to prevent slipping-down towards the lower part of the leg part 14 under the effect of the elastic return thereof. This return is the result in particular of its having been stretched in the longitudinal direction and of the various movements and stresses experienced by the orthosis in the service position, namely when being worn by the patient. Such slipping-down would effectively cause the desired therapeutic effect to disappear.

For this reason, the ribbed top 16 locally exerts a position-holding textile pressure.

Too low a position-holding textile pressure, like that applied by the ribbed top of a "fashion" sock, would be good for comfort, and therefore for patient observance but would not allow satisfactory position-holding in many situations.

Too high a textile position-holding pressure would ensure that the orthosis is held correctly on the leg under all circumstances, but would create discomfort for the patient or might even locally introduce striction or occlusion of the veins.

The pressure exerted by the ribbed top conventionally takes account of the pressure exerted by the leg part.

Intermediate Part

The intermediate part 18 extends the leg part 14.

For preference, the same weft inlay yarn is used for the leg part and for the intermediate part.

For preference, the same body knit yarn is also used for the leg part and for the intermediate part.

For preference, the intermediate part 18 is knitted in continuity with the leg part 14. In other words, this is not a part that is added on but a part that is knitted as part of the same knitting sequence on the knitting machine. On crossing the boundary between the leg part 14 and the intermediate part 18 there is therefore no change in weft inlay yarn and neither is there any change in body knit yarn.

In one embodiment, the only difference between the leg part and the intermediate part is in the stitch type.

In one preferred embodiment, on crossing the boundary between the leg part and the intermediate part, the textile pressure increases by less than 20%, preferably by less than 10% and/or by more than 2%, preferably by more than 5% with respect to the textile pressure on the side of the leg part. The continuity of textile pressure considerably improves the comfort to the wearer.

The textile pressure exerted by the intermediate part is dependent on the pressure exerted in order to hold the orthosis in the service position. This pressure is dependent on the structure of the leg part and on the coefficient of friction of the leg part. The position-holding pressure is also dependent on the length of the leg part. Through simple tests, a person skilled in the art knows how to determine a structure for the intermediate part that is suited to a particular leg part.

The intermediate part 18 preferably comprises ribs 30 extending preferably substantially vertically. The ribs 30 preferably extend over the entire contour of the intermediate part, as depicted. The width of each rib is preferably greater than 0.5 mm, greater than 1 mm and/or less than 10 mm or less than 5 mm.

In one embodiment, the orthosis has
- a simple inlaid jersey stitch, for the leg part 14, giving it a smooth appearance; and
- a jersey stitch with a ribbed pattern for the intermediate part 18, for example a 1×1 jersey rib pattern (which means to say with 1 wale raised ×1 wale recessed, corresponding to a knit with 1 stitch in place 1, ×1 purl stitch).

Advantageously, this structure leads to:
- a slightly ribbed appearance in the intermediate part 18, which is highly satisfactory from an aesthetic standpoint, comparable with the appearance of a conventional "fashion" sock; and
- a very good continuity of pressure profile, the two, leg and intermediate, parts being produced using the same body knit and weft inlay yarns, with no interruption to the process on the knitting machine.

In one embodiment, the discontinuity of the pressure profile on crossing the boundary between the leg part and the intermediate part is less than 10%, preferably less than 5%, preferably less than 2% of the pressure exerted by the leg part near the said boundary.

In one preferred embodiment, there is no discontinuity in the pressure profile at the transition between the leg part and the intermediate part.

In one embodiment, the discontinuity in pressure is the result only of a change in stitch type between the leg part and the intermediate part.

The continuity of the pressure profile advantageously improves comfort for the patient.

The 1×1 ribbed pattern also allows the orthosis to maintain circumferential elasticity in the intermediate part 18 where the ribs 30 form pleats that can easily be stretched out. Advantageously, the ribs 30 also make it possible to reduce substantially the tendency of the knit to roll up on itself or form wrinkles.

The height H of the intermediate part is preferably greater than 2.0 cm, preferably greater than 3.0 cm, preferably greater than 4.0 cm, and/or preferably less than 8.0 cm, preferably less than 6.0 cm, preferably less than 5.0 cm.

The structure of the intermediate part is determined in the conventional way such that the intermediate part, in collaboration with the leg part, holds the orthosis in the service position. The textile pressure exerted by the intermediate part may be determined without taking account of the textile pressure exerted by the welt, the chief function of the welt being to prevent the upper edge of the orthosis from rolling over on itself.

Welt

The intermediate part 18 is extended, on the opposite side to the leg part, by the welt 20, namely by a folding-over of the neck of the orthosis (which defines the opening via which the orthosis is put on) outwards or, for preference, towards the inside of the orthosis. The welt 20 thus comprises an inner band, intended to be in contact with the skin of the lower limb of the patient, and an outer band which is exposed on the outside and isolated from the skin by the inner band.

For preference, the same yarn is used for the body knit yarns of the intermediate part and of the welt, and, for preference, the same yarn is used for the body knit yarns of the leg part, of the intermediate part and of the welt. The preferred features described hereinabove for the body knit yarn of the leg part, notably as far as the titres and constituent materials are concerned, therefore apply to the body knit yarn of the welt. For preference, the body knit yarn of the welt 20 is a yarn comprising a 17 dTex elastane core single wrapped with a 42 dTex polyamide yarn.

The stitches knitted with the body knit yarn of the welt 20 may be identical to or different from the stitches knitted with the body knit yarn of the intermediate part 18. For preference, the stitches used in the welt 20 are identical to the stitches used in the intermediate part 18. For preference, the stitches used in the welt 20 are jersey stitches.

In one embodiment, the welt is formed in the continuity of the intermediate part, the only change in the manufacturing process being to eliminate or modify the weft inlay yarn.

Figures 4A, 4B:
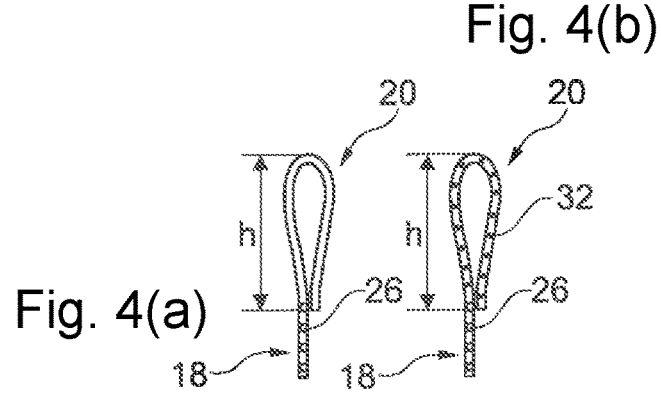
FIGS. 4(a), 4(b), and 4(c) illustrate three possible alternative forms of embodiment of the welt in the ribbed top of an orthosis of the invention.
Figure 4C:
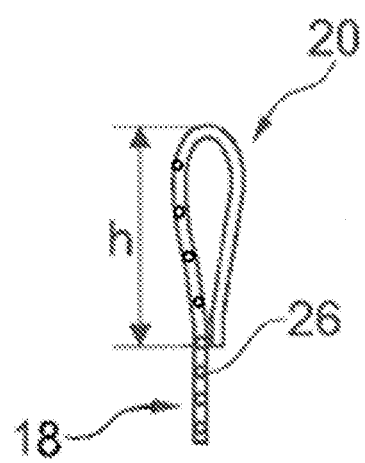

FIGS. 4(*a*), 4(*b*), and 4(*c*) illustrate three preferred embodiments of the welt 20.

In the first preferred embodiment illustrated in FIG. 4(*a*), the welt has no weft inlay yarn. It has a smooth appearance. The weft inlay yarn therefore does not extend beyond the intermediate part 18.

On crossing the boundary between the intermediate part 18 and the welt 20, the knit is preferably continued on the knitting machine with no change in body knit yarn, but by eliminating the weft inlay yarn.

In the second preferred embodiment illustrated in FIG. 4(*b*), the welt 20 comprises a weft inlay yarn 32 that is different from the weft inlay yarn 26 used in the leg part 14 and the intermediate part 18. For this, a weft inlay yarn 32 has been chosen that is preferably less "nervous" than the weft inlay yarn 26, preferably with a lower titre.

In the third preferred embodiment illustrated in FIG. 4(*c*), the welt has a weft inlay yarn only on one of the inner band and the outer band.

For preference, the ratio
- of the titre of the core of the weft inlay yarn of the intermediate part or, if the weft inlay yarn of the intermediate part is not wrapped, of the titre of the weft inlay yarn of the intermediate part.
- to the titre of the core of the weft inlay yarn 32 of the welt 20 or, if the weft inlay yarn 32 is not wrapped, to the titre of the weft inlay yarn 32, is greater than 1.5, preferably greater than 1.9, preferably greater than 2.0, preferably greater than 2.1, preferably greater than 2.2, preferably greater than 2.3, and/or less than 3.0, preferably less than 2.8, preferably less than 2.6, preferably less than 2.5, preferably less than 2.4.

The weft inlay yarns of the intermediate part and of the welt are preferably chosen so that the textile pressure exerted by the welt 20 (taking its double thickness into account) on average over the surface of the welt (surface area in contact with the skin) is less than or equal to, preferably more than 1%, more than 3%, more than 5% less than that applied, on average, by the intermediate part 18.

For preference also, the welt is knitted in such a way that on crossing the boundary from the intermediate part to the welt, the textile pressure remains constant or decreases, preferably by more than 1%, more than 2%, more than 5%, or even more than 10%.

Comfort is thereby advantageously maximized, and the risk of striction minimized.

In one embodiment, there is substantially no discontinuity of the textile pressure profile when crossing the said boundary.

For preference, the weft inlay yarn 32 of the welt 20 is wrapped, preferably double wrapped.

For preference, the titre of the core of the weft inlay yarn 32 of the welt 20 is less than 150 dTex, preferably less than 140 dTex, preferably less than 135 dTex, and/or greater than 100 dTex, preferably greater than 110 dTex, preferably greater than 120 dTex, preferably greater than 125 dTex.

For preference, the titre of the gimping yarn with which the weft inlay yarn 32 of the welt 20 is wrapped is less than 40 dTex, preferably less than 30 dTex, preferably less than 25 dTex, and/or greater than 10 dTex, preferably greater than 15 dTex, preferably greater than 20 dTex.

The weft inlay yarn 32 of the welt 20 preferably comprises a core, the titre of which is 130 dTex, preferably double wrapped with a gimping yarn, the titre of which is 22 dTex. The core is preferably made of elastane. The gimping yarn is preferably made of polyamide.

In another embodiment, it is possible for a weft inlay yarn to be present only in part of the welt, for example only over part of the height of the welt or only in one band, for example the outer band, of the welt 20.

The height h of the welt is preferably less than 1.0 cm, preferably less than 0.8 mm, and/or greater than 1 mm, greater than 3 mm.

Specifically, because the welt 20 plays little part in holding the orthosis in position, this position-holding being performed chiefly by the intermediate part 18, its height h may be small.

The small height h provides an advantageous aesthetic appearance: indeed, the welt forms a discrete line at the end of the orthosis, which is itself preferably knitted in a single thickness.

Finally, the structure of the orthosis can be achieved with ease, with high productivity and with no complex programming or interruption to the knitting sequence, on a conventional knitting machine of the single cylinder type.

The gauge is preferably greater than 14, preferably greater than 20, preferably greater than 24, preferably greater than 25, and/or less than 35, preferably less than 30, the gauge being the number of needles along a cylinder arc measuring one inch.

The number of needles along a cylinder arc measuring one centimetre is preferably greater than 7, preferably greater than 9, preferably greater than 10 and/or less than 14, preferably less than 12.

A high gauge, possible thanks to the use of a knitting machine of the single cylinder type, advantageously allows a fine, more comfortable, structure.

Of course, the invention is not limited to the embodiments described and depicted, which are given for illustrative purposes only.

In particular, beyond the portion of the leg part that defines the boundary with the intermediate part, the leg part could exhibit variations. For example, the body knit yarn used in the leg part may be the same or different according to the portion of the leg part considered.

The invention claimed is:

1. Orthosis chosen from a venous support orthosis and an elastic venous compression orthosis, and comprising a ribbed top and a leg part, the ribbed top comprising
   an intermediate part comprising ribs and extending the leg part, the leg part and the intermediate part having a leg part stitch and an intermediate part stitch, respectively, and being separated by a boundary, the leg part stitch being different than the intermediate part stitch on each side of the boundary separating the leg part and the intermediate part,
   a welt, said welt being a folding-over of a neck of the orthosis which defines an opening via which the orthosis is put on, and thus comprising an inner band, intended to be in contact with a skin of a lower limb of a patient, and an outer band which is exposed on an outside of the orthosis and isolated from the skin by the inner band, said welt extending the intermediate part and having a height less than 1.5 cm,
   wherein the textile pressure increases by less than 20% and by more than 2% upon crossing the boundary between the leg part and the intermediate part.

2. Orthosis according to claim 1, in which the welt is knitted in such a way that on crossing the boundary from the intermediate part to the welt part, the textile pressure remains constant or decreases.

3. Orthosis according to claim 1, in which the welt is chosen so that the textile pressure exerted by the welt is less than the pressure applied, on average per $cm^2$, by the leg part.

4. Orthosis according to claim 1, in which the intermediate part is knitted with body knit and weft inlay yarns and the leg part is knitted with said body knit and weft inlay yarns.

5. Orthosis according to claim 1, in which the welt has a weft inlay yarn only in part of the welt.

6. Orthosis according to claim 1, in which
   the leg part has a jersey stitch giving a smooth appearance; and
   the intermediate part has a jersey stitch giving a ribbed pattern.

7. Orthosis according to claim 1, in which the intermediate part has a height (H) greater than 3.0 cm and less than 8.0 cm.

8. Orthosis according to claim 1, in which the welt is knitted with a body knit yarn and the intermediate part is knitted with said body knit yarn.

9. Orthosis according to claim 1, in which the welt has no weft inlay yarn or comprises a weft inlay yarn different from a weft inlay yarn of the intermediate part.

10. Orthosis according to claim 1, of class I, II, III or IV according to the ASQUAL standard classification system.

11. Orthosis according to claim 1, in which on crossing the boundary between the leg part and the intermediate part, the textile pressure increases by less than 10% and/or by more than 5%.

12. Orthosis according to claim 1, in which the welt has a weft inlay yarn only on one of said inner band and said outer band.

13. Orthosis according to claim 1, in which the welt is chosen so that the textile pressure exerted by the welt is less than the pressure applied, on average per $cm^2$, by the intermediate part.

14. Orthosis according to claim 1, in which the welt is chosen so that the textile pressure exerted by the welt is less than the pressure applied, on average per $cm^2$, by the leg part and by the intermediate part.

15. Orthosis according to claim 1, in which the welt has a height (h) less than 1.0 cm.

16. Method of manufacturing an orthosis according to claim 1, in which use is made of a circular knitting machine of the "single cylinder" type.

17. Method according to claim 16, in which the circular knitting machine of the "single cylinder" type has a gauge greater than 20, the gauge being the number of needles along a cylindrical arc measuring one inch.

* * * * *